(12) United States Patent
Murry, III et al.

(10) Patent No.: US 8,986,372 B2
(45) Date of Patent: Mar. 24, 2015

(54) TRANSCATHETER PROSTHETIC HEART VALVE DELIVERY SYSTEM WITH FUNNEL RECAPTURING FEATURE AND METHOD

(71) Applicant: Medtronic, Inc., Minneapolis, MN (US)

(72) Inventors: Robert Murry, III, Santa Rosa, CA (US); Susheel Deshmukh, Santa Rosa, CA (US); Padraig Savage, Limerick (IE); Matthew Rust, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 31 days.

(21) Appl. No.: 13/969,784

(22) Filed: Aug. 19, 2013

(65) Prior Publication Data

US 2014/0012369 A1    Jan. 9, 2014

Related U.S. Application Data

(62) Division of application No. 12/758,443, filed on Apr. 12, 2010, now Pat. No. 8,512,401.

(51) Int. Cl.
*A61F 2/24* (2006.01)
*A61F 2/95* (2013.01)

(52) U.S. Cl.
CPC ....... *A61F 2/2436* (2013.01); *A61F 2002/9517* (2013.01); *A61F 2002/9534* (2013.01)
USPC ........................................ 623/2.11

(58) Field of Classification Search
CPC .............. A61F 2002/9528; A61F 2/95; A61F 2002/9534; A61B 2017/2215; A61B 17/221
USPC ........ 623/1.11, 2.1, 2.11, 2.12; 606/108, 191, 606/194, 198, 200
See application file for complete search history.

(56) References Cited

U.S. PATENT DOCUMENTS

| 4,997,435 | A | 3/1991 | Demeter |
| 5,312,417 | A | 5/1994 | Wilk |
| 5,683,451 | A | 11/1997 | Lenker et al. |
| 5,707,359 | A | 1/1998 | Bufalini |
| 5,749,921 | A | 5/1998 | Lenker et al. |
| 5,755,724 | A | 5/1998 | Yoon |
| 5,800,457 | A | 9/1998 | Gelbfish |
| 5,824,041 | A | 10/1998 | Lenker et al. |

(Continued)

FOREIGN PATENT DOCUMENTS

| GB | 2433700 | 7/2007 |
| WO | WO2008/138584 | 11/2008 |
| WO | WO2009/091509 | 7/2009 |

*Primary Examiner* — Katherine M Shi

(57) ABSTRACT

A delivery device for percutaneously deploying a stented prosthetic heart valve. The device includes a delivery capsule and a recapture sheath. The capsule is configured to compressively retain the prosthesis. The recapture sheath includes a funnel segment having a plurality of circumferentially spaced runners and a polymer overlay. The runners are attached to a shaft and terminate at a distal tip. The overlay surrounds the runners, and is bonded to the shaft but not to at least the tips. The funnel segment is transitionable from a normal condition to an expanded condition forming a funnel shape with a distally increasing diameter, and self-transitionable back toward the normal condition. The funnel segment facilitates sliding of the capsule over a partially deployed region of the prosthesis as part of a recapturing operation. The runners provide columnar strength, with the overlay controlling a shape of the funnel segment.

7 Claims, 9 Drawing Sheets

(56) References Cited

U.S. PATENT DOCUMENTS

| | | |
|---|---|---|
| 5,906,619 A | 5/1999 | Olson et al. |
| 5,957,949 A | 9/1999 | Leonhardt et al. |
| 6,156,055 A | 12/2000 | Ravenscroft |
| 6,241,738 B1 | 6/2001 | Dereume |
| 7,837,692 B2 | 11/2010 | Mulholland et al. |
| 2003/0199963 A1 | 10/2003 | Tower et al. |
| 2005/0137688 A1 | 6/2005 | Salahieh et al. |
| 2006/0004439 A1 | 1/2006 | Spenser et al. |
| 2006/0052867 A1 | 3/2006 | Revuelta et al. |
| 2006/0259136 A1 | 11/2006 | Nguyen et al. |
| 2006/0265056 A1 | 11/2006 | Nguyen et al. |
| 2007/0005131 A1 | 1/2007 | Taylor |
| 2007/0088431 A1 | 4/2007 | Bourang et al. |
| 2007/0239254 A1 | 10/2007 | Chia et al. |
| 2007/0239266 A1 | 10/2007 | Birdsall |
| 2007/0239269 A1 | 10/2007 | Dolan et al. |
| 2007/0270932 A1 | 11/2007 | Headley et al. |
| 2008/0065011 A1 | 3/2008 | Marchand et al. |
| 2008/0082165 A1 | 4/2008 | Wilson et al. |
| 2008/0147160 A1 | 6/2008 | Ghione et al. |
| 2008/0147181 A1 | 6/2008 | Ghione et al. |
| 2008/0188928 A1 | 8/2008 | Salahieh et al. |
| 2009/0093876 A1 | 4/2009 | Nitzan et al. |
| 2009/0138079 A1 | 5/2009 | Tuval et al. |
| 2009/0171447 A1 | 7/2009 | von Segesser et al. |
| 2009/0171456 A1 | 7/2009 | Kveen et al. |
| 2009/0177275 A1 | 7/2009 | Case |
| 2009/0281619 A1 | 11/2009 | Le et al. |
| 2010/0049313 A1 | 2/2010 | Alon et al. |
| 2010/0094411 A1 | 4/2010 | Tuval et al. |
| 2010/0121434 A1 | 5/2010 | Paul et al. |

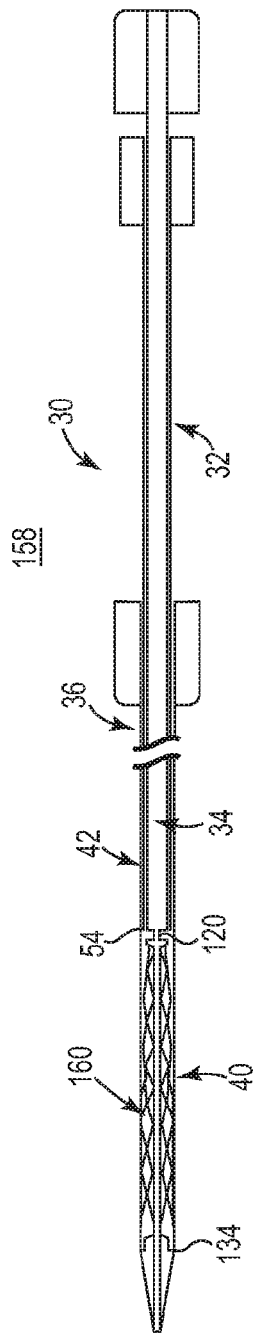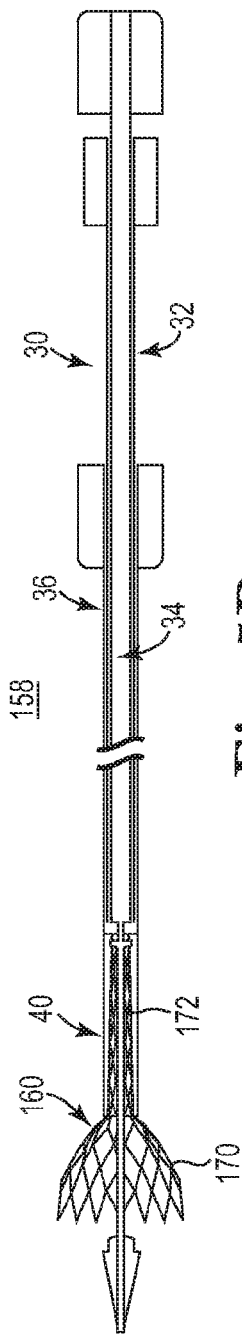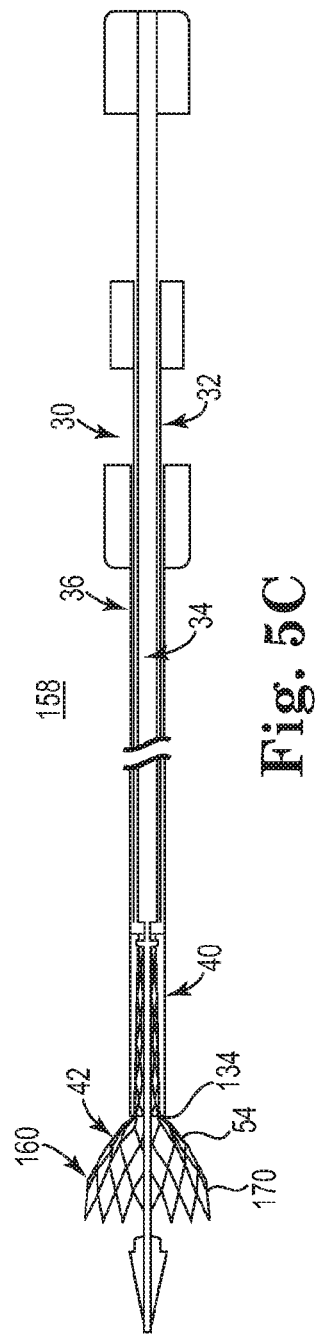

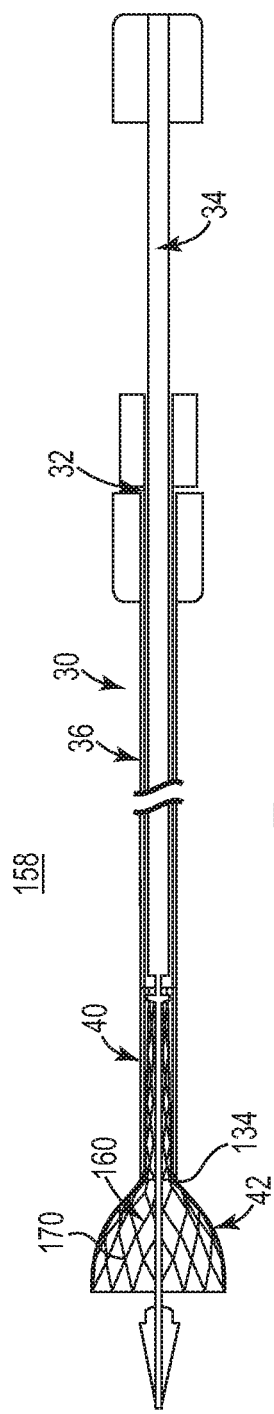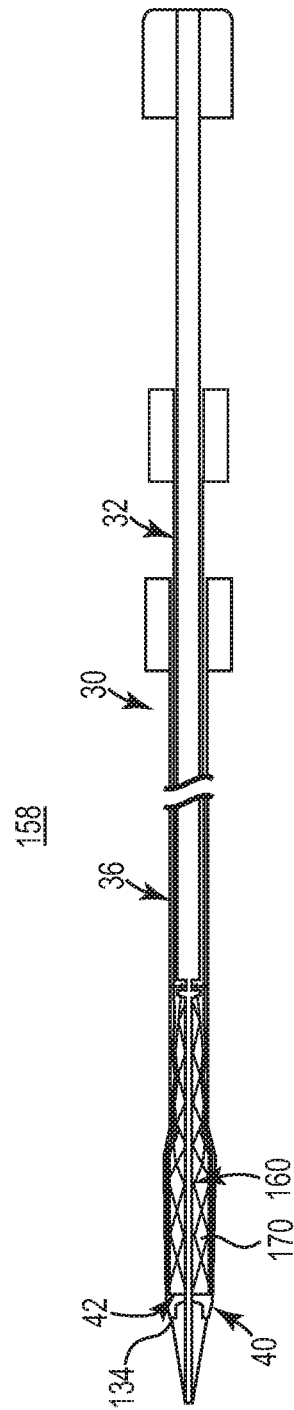

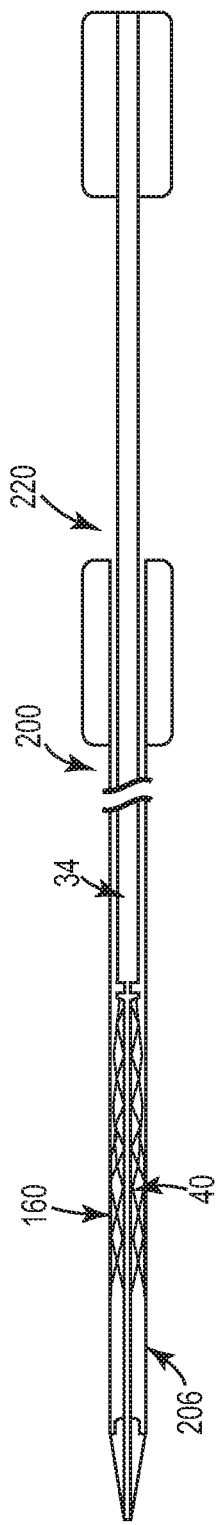
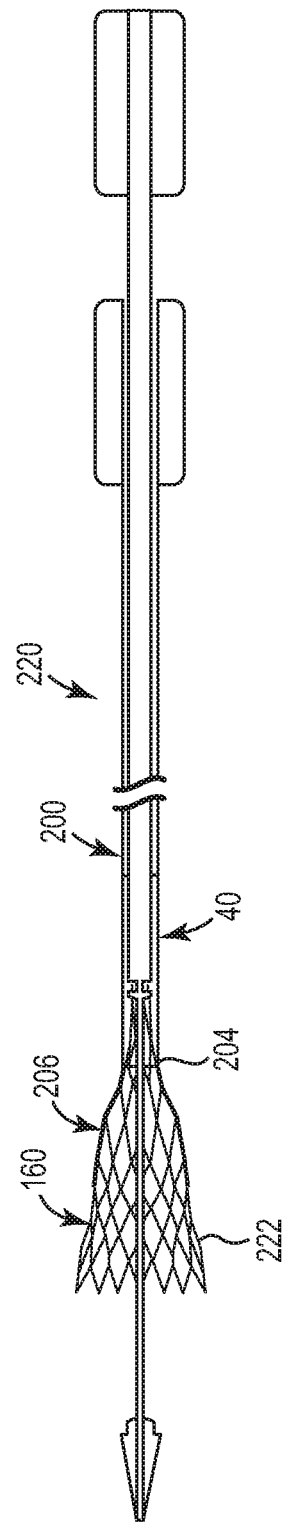

TRANSCATHETER PROSTHETIC HEART VALVE DELIVERY SYSTEM WITH FUNNEL RECAPTURING FEATURE AND METHOD

RELATED APPLICATIONS

This application is a Division of and claims the benefit of U.S. patent application Ser. No. 12/758,443 filed Apr. 12, 2010, now allowed. The disclosures of which are herein incorporated by reference in their entirety.

BACKGROUND

The present disclosure relates to systems, devices, and methods for percutaneous implantation of a heart valve prosthesis. More particularly, it relates to systems, devices, and methods for transcatheter implantation of a stented prosthetic heart valve, including partial deployment, recapturing, and repositioning of the prosthesis at the implantation site.

Diseased or otherwise deficient heart valves can be repaired or replaced with an implanted prosthetic heart valve. The terms "repair" and "replace" are used interchangeably throughout the specification, and a reference to "repair" of a defective native heart valve is inclusive of a prosthetic heart valve that renders the native leaflets non-functional, or that leaves the native leaflets intact and functional. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be restored (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

Various types and configurations of prosthetic heart valves are available for percutaneous valve replacement procedures, and continue to be refined. The actual shape and configuration of any particular prosthetic heart valve is dependent to some extent upon the native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent is made of a self-expanding material and construction. With these devices, the valved stent is crimped down to a desired size and held in that compressed arrangement within an outer sheath, for example. Retracting the sheath from the valved stent allows the stent to self-expand to a larger diameter, such as when the valved stent is in a desired position within a patient. In other percutaneous implantation devices, the valved stent can be initially provided in an expanded or uncrimped condition, then crimped or compressed on a balloon portion of catheter until it is as close to the diameter of the catheter as possible. Once delivered to the implantation site, the balloon in inflated to deploy the prosthesis. With either of these types of percutaneous stented prosthetic heart valve delivery devices, conventional sewing of the prosthetic heart valve to the patient's native tissue is typically not necessary.

It is imperative that the stented prosthetic heart valve be accurately located relative to the native annulus immediately prior to full deployment from the catheter as successful implantation requires the prosthetic heart valve intimately lodge and seal against the native annulus. If the prosthesis is incorrectly positioned relative to the native annulus, serious complications can result as the deployed device can leak and may even dislodge from the native valve implantation site. As a point of reference, this same concern does not arise in the context of other vascular stents; with these procedures, if the target site is "missed," another stent is simply deployed to "make-up" the difference.

While imaging technology can be employed as part of the implantation procedure to assist a clinician in better evaluating a location of the transcatheter prosthetic heart valve immediately prior to deployment, in many instances, this evaluation alone is insufficient. Instead, clinicians desire the ability to partially deploy the prosthesis, evaluate a position relative to the native annulus, and then reposition the prosthesis prior to full deployment if deemed necessary. Repositioning, in turn, requires the prosthesis first be re-compressed and re-located back within the outer delivery sheath. Stated otherwise, the partially deployed stented prosthetic heart valve must be "recaptured" by the delivery device, and in particular within the outer sheath. While, in theory, the recapturing of a partially deployed stented prosthetic heart valve is straight forward, in actual practice, the constraints presented by the implantation site and the stented heart valve itself render the technique exceedingly difficult.

For example, the stented heart valve is purposefully designed to rigidly resist collapsing forces once deployed to properly anchor itself in the anatomy of the heart. Thus, the delivery device component (e.g., outer delivery sheath) employed to force a partially-deployed segment of the prosthesis back to a collapsed arrangement must be capable of exerting a significant radial force. Conversely, however, the component cannot be overly rigid so as to avoid damaging the transcatheter heart valve as part of a recapturing procedure. Along these same lines, the aortic arch must be traversed, necessitating that the delivery device provide sufficient articulation attributes. Unfortunately, existing delivery devices do not consider, let alone optimally address, these and other issues.

As mentioned above, an outer sheath or catheter is conventionally employed to deliver a self-deploying vascular stent. Applying this same technique for the delivery of a self-deploying stented prosthetic heart valve, the high radial expansion force associated with the prosthesis is not problematic for complete deployment as the outer sheath is simply retracted in tension to allow the prosthetic heart valve to deploy. Were the conventional delivery device operated to only partially withdraw the outer sheath relative to the prosthesis, only the so-exposed distal region of the prosthetic would expand while the proximal region remained coupled to the delivery device. In theory, the outer sheath could simply be advanced distally to recapture the expanded region. Unfortunately, with conventional sheath configurations, attempting to compress the expanded region of the stented prosthetic heart valve by distally sliding the sheath is unlikely to be successful. The conventional delivery sheath cannot readily overcome the radial force of the expanded region of the prosthesis because, in effect, the sheath is placed into compression and will collapse due at least in part to the abrupt edge of the sheath being unable to cleanly slide over the expanded region of the prosthesis. This effect is illustrated in a simplified form in FIGS. 1A-1C. Prior to deployment (FIG. 1A), the stented prosthetic heart valve P is constrained within, and supports, the sheath S. With deployment (FIG. 1B), the sheath S is distally retracted, and the prosthesis P partially deploys. Were an attempt made to "recapture" the prosthesis P by distally sliding the sheath (FIG. 1C), a leading end E of the sheath S would abruptly abut against the enlarged diameter of the prosthesis P, such that the distal end E cannot readily slide over the prosthesis P. Further, the sheath S is no longer internally supported and the radially expanded bias of the prosthesis P will cause the sheath S to buckle or collapse.

In light of the above, a need exists for a stented transcatheter prosthetic heart valve delivery system, device, and method that satisfies the constraints associated with heart valve implantation and permits partial deployment and recapturing of the prosthesis.

SUMMARY

Some aspects in accordance with principles of the present disclosure relate to a delivery system for percutaneously deploying a stented prosthetic heart valve. The prosthetic heart valve is radially self-expandable from a compressed arrangement to a natural arrangement. The delivery device includes an inner shaft assembly, a delivery sheath capsule, and a recapture sheath. The inner shaft assembly includes an intermediate region providing a coupling structure configured to selectively engage a stented prosthetic heart valve. The delivery sheath capsule is slideably disposed over the inner shaft assembly and is configured to compressively retain a stented prosthetic heart valve. The recapture sheath is slideably disposed over the inner shaft assembly and includes a funnel segment extending distally from a shaft. The funnel segment includes a plurality of circumferentially spaced runners and a polymer overlay. The runners are each attached at a first end to the shaft and terminate at a distal tip opposite the shaft. The polymer overlay surrounds the runners. In this regard, the overlay is bonded to the shaft, but is not bonded to at least the distal tips. The funnel segment is transitionable from a natural condition to an expanded condition in which the funnel segment has a funnel shape with a distally increasing diameter. Further, the funnel segment is self-transitionable from the expanded condition toward the natural condition. With this construction, the delivery device is configured to provide a delivery state in which the capsule compressively retains the stented prosthetic heart valve over the inner shaft assembly and the funnel segment is longitudinally displaced from the prosthetic heart valve. During use, the funnel segment can be employed to facilitate sliding of the capsule over a partially deployed region of the prosthetic heart valve as part of a recapturing operation. In some embodiments, the recapture sheath is provided apart from the delivery sheath capsule and is slideably disposed between the delivery sheath capsule and the inner shaft assembly. In other embodiments, the funnel segment is formed as a distal extension from the delivery sheath capsule, with the funnel segment being located distal the prosthetic heart valve in the delivery state. Regardless, the runners provide a columnar strength to the funnel segment, with the overlay controlling a shape of the funnel segment when subjected to an internal expansion force, such as when the funnel segment slides over a partially deployed prosthetic heart valve.

Yet other aspects in accordance with principles of the present disclosure relate to a system for repairing (e.g., replacing) a heart valve of a patient. The system includes a delivery device and a prosthetic heart valve. The delivery device includes the inner shaft assembly, the delivery sheath capsule, and the recapture sheath, including the funnel segment, as described above. The prosthetic heart valve has a stent frame and a valve structure forming at least two valve leaflets attached to the frame. The prosthetic heart valve is self-expandable from a compressed arrangement to a natural arrangement. With this construction, the system is configured to be transitionable between a loaded mode, a partially deployed mode, and a recapturing mode. In the loaded mode, the prosthetic heart valve is coupled to the intermediate region of the inner shaft assembly, with the capsule compressively retaining the prosthetic heart valve in the compressed arrangement. Further, the funnel segment is longitudinally spaced from the prosthetic heart valve. In the partially deployed mode, the capsule is partially withdrawn from the prosthetic heart valve such that a distal region of the prosthetic heart valve is exposed relative to the capsule and self-expands. In the recapturing mode, the funnel segment is positioned distal the capsule and along the distal exposed region of the prosthetic heart valve, causing the funnel segment to expand toward the expanded condition.

Yet other aspects in accordance with principles of the present disclosure relate to a method of deploying a stented prosthetic heart valve to an implantation site. The method includes receiving a delivery device loaded with a radially expandable prosthetic heart valve having a stent frame to which a valve structure is attached. The delivery device includes a delivery sheath capsule compressively containing the prosthetic heart valve in a compressed arrangement over an inner shaft assembly in a delivery state, as well as a recapture sheath including a funnel segment slideably disposed over the inner shaft assembly. In the delivery state, the funnel segment is longitudinally spaced from the prosthetic heart valve. The prosthetic heart valve is delivered, in the compressed arrangement, through a bodily lumen of the patient and to the implantation site via the delivery device in the delivery state. The capsule is proximally retracted relative to the prosthetic heart valve such that a distal region of the prosthetic heart valve is exposed distal the capsule. The exposed, distal region self-expands toward a natural arrangement. A position of the partially deployed prosthetic heart valve relative to the implantation site is evaluated. Based upon the evaluation, the recapture sheath is distally advanced relative to the prosthetic heart valve such that the funnel segment is distal the capsule and expands to a funnel shape in response to contact with the distal region of the prosthetic heart valve. The funnel segment is distally advanced over the distal region of the prosthetic heart valve. The capsule is then arranged over the prosthetic heart valve to cause the distal region to transition back toward the collapsed arrangement within the capsule. Finally, the capsule and the funnel segment are fully proximally retracted from the prosthetic heart valve such that the prosthetic heart valve deploys from the inner shaft assembly. In some embodiments, the recapture sheath is slideably disposed within the delivery sheath such that recapturing of the partially deployed prosthetic heart valve includes sliding the funnel segment over the prosthetic heart valve, followed by sliding of the capsule over the funnel segment. In other embodiments, the funnel segment is provided as a distal extension from the capsule such that recapturing of the prosthetic heart valve includes sliding of the funnel segment over the prosthetic heart valve sequentially followed by sliding of the capsule over the prosthetic heart valve.

BRIEF DESCRIPTION OF THE DRAWINGS

FIGS. 5A-5E are simplified, cross-sectional views illustrating use of a system for repairing (e.g., replacing) a defective heart valve of a patient in accordance with the present disclosure, including using the delivery device of FIG. 2 to deliver, partially deploy and recapture a stented prosthetic heart valve;

FIG. 7 is a simplified side cross-sectional view of another system in accordance with the present disclosure and including a delivery device incorporating the delivery sheath assembly of FIG. 6 loaded with a stented prosthetic heart valve; and FIGS. 8A and 8B are simplified cross-sectional views illustrating operation of the system of FIG. 7 in delivering a stented prosthetic heart valve to an implantation site, including partially deploying and recapturing the prosthesis.

DETAILED DESCRIPTION

Figure 1A:
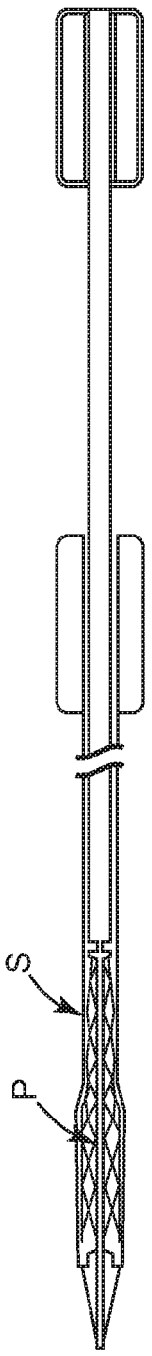
FIGS. 1A-1C are simplified side views illustrating deficiencies of existing stent delivery sheaths or catheters to effectuate recapture of a partially deployed stented prosthetic heart valve.
Figure 1B:
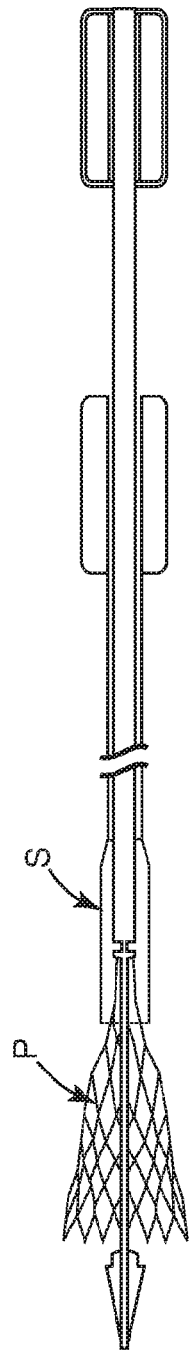
Figure 1C:
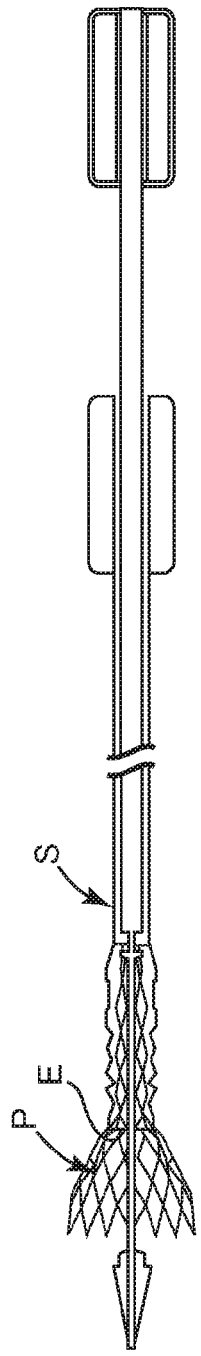

Current transcatheter heart valve delivery devices do not have the capability of transcatheter valve repositioning in the antegrade or retrograde directions after deployment. The delivery devices of the present disclosure overcome these problems, and permit the clinician to partially deploy the prosthetic heart valve, and prior to release, recapture and reposition or remove it. In general terms, the device functions by providing a recapture sheath having a funnel segment that serves as a transition between the delivery sheath capsule and an expanded region of a partially deployed prosthesis to effectuate recapturing of the partially deployed prosthetic heart valve within the delivery sheath capsule.

As referred to herein, the stented prosthetic heart valve as used in accordance with the various systems, devices, and methods of the present disclosure may include a wide variety of different configurations, such as a bioprosthetic heart valve having tissue leaflets or a synthetic heart valve having a polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a natural or normal, expanded arrangement and collapsible to a compressed arrangement for loading within the delivery device. The stent is normally constructed to self-deploy or self-expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a verity of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine paracardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from the compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the natural, expanded arrangement. In the collapsed arrangement, such a stent frame support structure with attached valves can be mounted onto a delivery device. The stent frame support structures are configured so that they can be changed to their natural, expanded arrangement when desired, such as by the relative movement of one or more sheaths relative to a length of the stent frame.

The wires of the stent frame support structures in embodiments of the present disclosure can be formed from a shape memory material such as a nickel titanium alloy (e.g., Nitinol™) With this material, the support structure is self-expandable from the compressed arrangement to the natural, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 2:
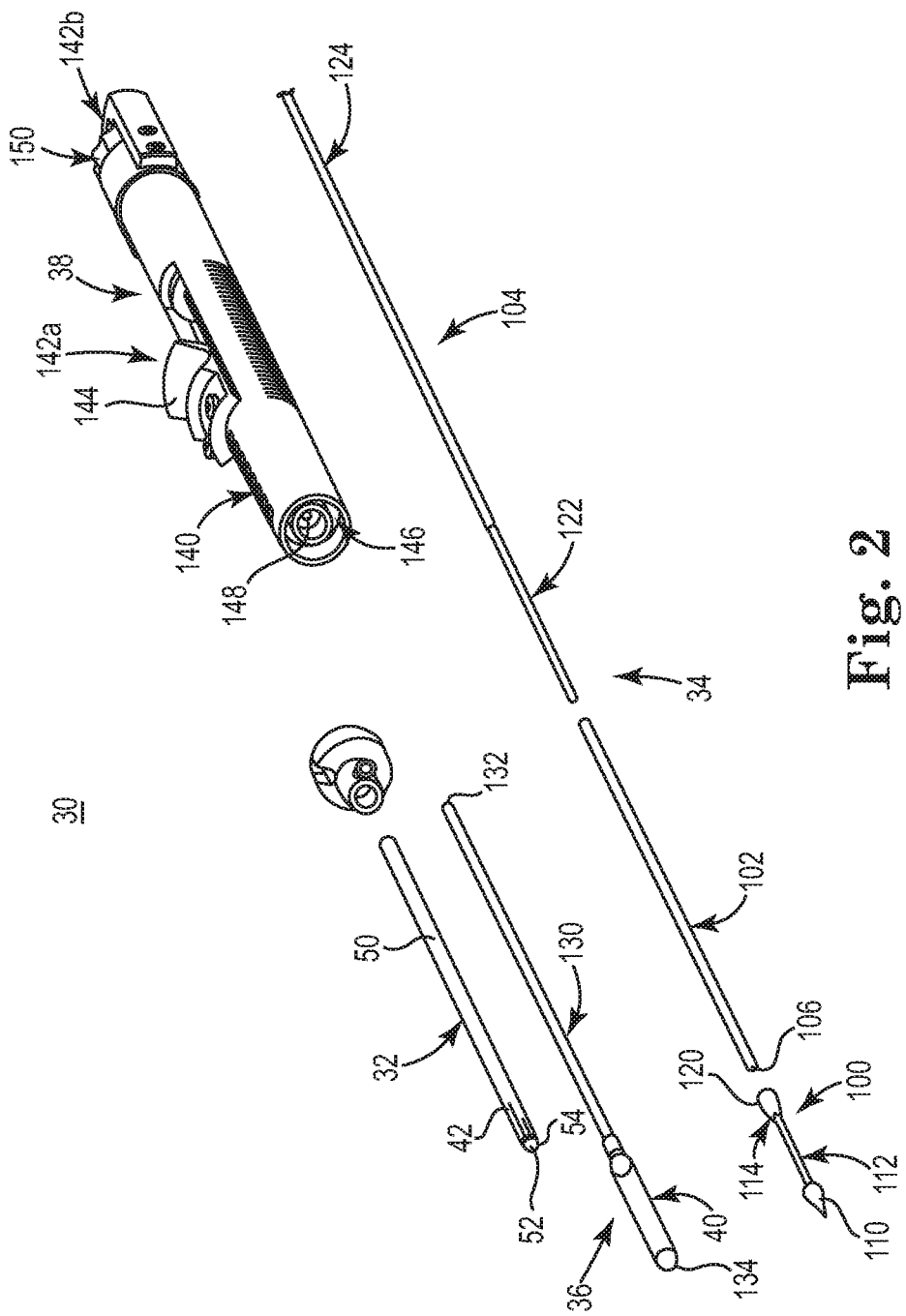
FIG. 2 is an exploded, perspective view of a delivery device in accordance with principles of the present disclosure and useful for percutaneously delivering a stented prosthetic heart valve to a heart valve implantation site.

With the above in mind, one embodiment of a transcatheter stented prosthetic heart valve delivery device 30 in accordance with principles of the present disclosure is shown in FIG. 2. The device 30 generally includes a recapture sheath 32, an inner shaft assembly 34, a delivery sheath assembly 36, and a handle 38. Details on the various components are provided below. In general terms, however, the delivery device 30 combines with a stented prosthetic heart valve (not shown) to form a system for repairing (e.g., replacing) a defective heart valve of a patient. The delivery device 30 provides a delivery state in which the stented prosthetic heart valve is coupled to the inner shaft assembly 34 and compressively retained within a capsule 40 of the delivery sheath assembly 36. The delivery sheath assembly 36 can be manipulated to withdraw the capsule 40 proximally from the prosthetic heart valve via operation of the handle 38, permitting the prosthesis to self-expand (alternatively be caused to expand) and release from the inner shaft assembly 34. Further, the handle 38 can be operated to maneuver the recapture sheath 32 relative to the inner shaft assembly 34 and the delivery sheath assembly 36 to position a funnel segment 42 of the recapture sheath 32 distally beyond the capsule 40 and over a partially deployed region of the prosthetic heart valve to facilitate recapturing of the prosthesis within the capsule 40.

Various features of the components 32-38 reflected in FIG. 2 and described below can be modified or replaced with differing structures and/or mechanisms. Thus, the present disclosure is in no way limited to the inner shaft assembly 34, the delivery sheath assembly 36, the handle 38, etc., as shown and described below. More generally, delivery devices in accordance with the present disclosure provide features capable of compressively retaining a self-deploying, stented prosthetic heart valve (e.g., the capsule 40), a mechanism capable of effectuating release or deployment of the prosthesis (e.g., retracting the capsule 40), and a funneling-type structure (e.g., the funnel segment 42) that promotes recapture.

The recapture sheath 32 includes the funnel segment 42 and a shaft 50, with the funnel segment 42 extending distal the shaft 50. The recapture sheath 32 forms a lumen 52 (referenced generally) sized to be slideably received over the inner shaft assembly 34, with the recapture sheath 32 terminating at a distal end 54. With the one construction of FIG. 2, the recapture sheath 32 is provided apart from the delivery sheath assembly 36, and is sized to be slideably received between the inner shaft assembly 34 and the delivery sheath assembly 36. In other embodiments described below, the recapture sheath 32 is provided as part of the delivery sheath assembly 36, with the funnel segment 42 being formed as a distal extension from the capsule 40.

Figure 3A:
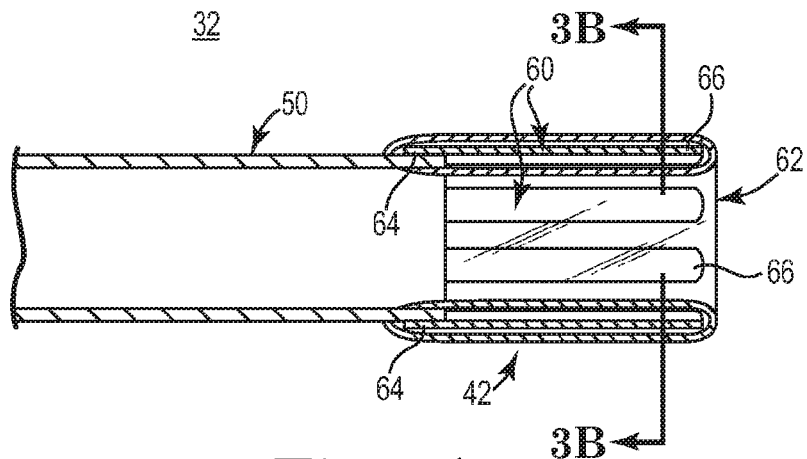
FIG. 3A is a simplified, enlarged, cross-sectional view of a portion of a recapture sheath component of the system of FIG. 2 and in a normal condition.
Figure 3B:
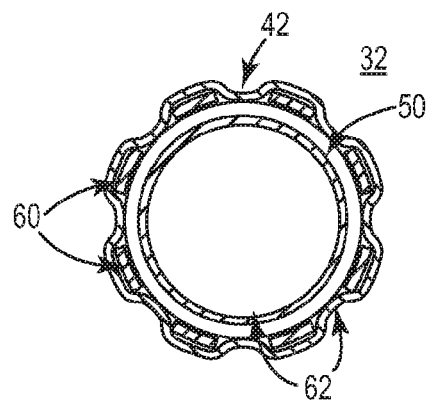
FIG. 3B is a transverse cross-sectional view of the recapture sheath of FIG. 3A, taken along the line 3B-3B.
Figure 3C:
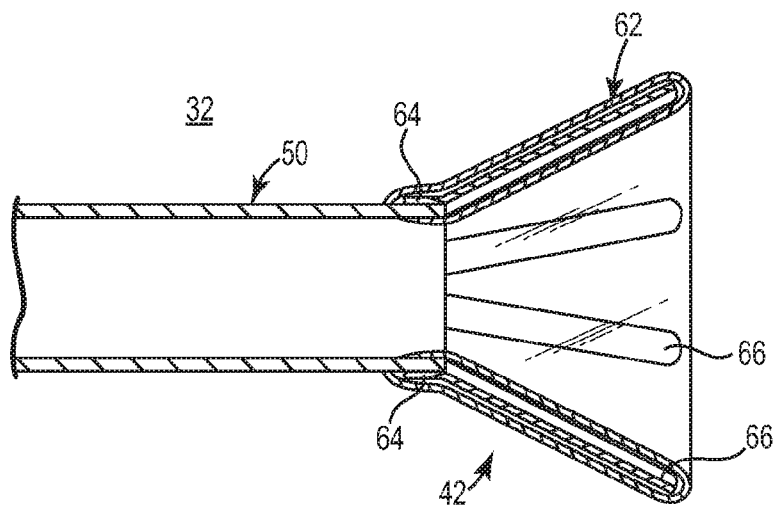
FIG. 3C is a side view of the recapture sheath portion of FIG. 3A in an expanded condition.

The funnel segment 42 is configured to be radially expandable (e.g., in response to an internally applied, radially expansive force) from the normal or relaxed condition of FIG. 2 having a relatively small, relatively uniform diameter (e.g., akin to a uniform diameter cylinder or tube) to an expanded condition having a flange or funnel-like shape in which a diameter of the distal end 54 is radially increased (as compared to the normal condition). Upon removal of the expansive force, the funnel segment 42 self-transitions from the expanded condition back to or toward the normal condition. As best shown in FIGS. 3A and 3B, in some embodiments the funnel segment 42 includes a plurality of circumferentially spaced runners 60 and a polymer overlay 62. A thickness of runners 60 and the overlay 62 is exaggerated in FIGS. 3A-3C for ease of explanation. Further the overlay 62 is illustrated as being transparent such that several of the runners 60 "behind" or within the overlay 62 in FIGS. 3A and 3C are visible. The runners 60 are identical in some constructions, each having a first end 64 attached to the shaft 50, and terminating at a distal tip 66 opposite the shaft 50. The polymer overlay 62 surrounds the runners 60, and controls transitioning or deflection of the runners 60 from the normal condition of FIGS. 3A and 3B to the expanded condition of FIG. 3C. The runners 60, in turn, impart a shape memory attribute to the funnel segment 42, and cause the funnel segment 42 to self-transition from the expanded condition of FIG. 3C toward the normal condition of FIG. 3A as described below.

The runners 60 are, in some embodiments, formed as flexible metal strips, such as thin, stainless steel or NiTi strips. The shape and construction of the runners 60 are such that each of the runners 60 normally assumes a relatively linear or flat shape, for example via an imparted shape memory attribute. The first end 64 of each of the runners 60 can be attached to the shaft 50 in a variety of manners, such as adhesive bonding, welding, etc. Apart from the shaft 50 and the overlay 62, the runners 60 are not interconnected. Thus, the runners 60 can freely deflect relative to one another, and in particular at the respective distal tips 66, to the extent permitted by the overlay 62, deflecting at the point of attachment with the shaft 50.

The funnel segment 42 can include two or more of the runners 60. In some embodiments, however, the funnel segment 42 includes at least four of the runners 60, with the runners 60 optionally being equidistantly spaced from one another about a circumference of the shaft 50. As shown, the distal tips 66 are, in some constructions, rounded, although other shapes are also envisioned. While the runners 60 can have a variety of differing dimensions, in some embodiments, each of the runners 60 has a thickness in the range of 0.005-0.015 inch and a length of extension from the shaft 50 to the corresponding distal tip 66 in the range of 0.20-1.0 inch.

The overlay 62 is a surgically safe, compliant polymeric material or film wrapped about the runners 60 and bonded to the shaft 50. For example, the overlay 62 can be or include nylon or other amid block polymer, urethane, polyester, aliphatic polyamides, copolymers of polyether and polyamide, plasticized polyamides containing a sulfonamide plasticizer, thermoplastic polyether urethanes, low density or linear low density polyethylenes (that may or may not be cross-linked), etc. The overlay material(s) can be biaxially oriented. Further, the overlay 62 can have a single, dual, or multi-layer construction. In some embodiments, the overlay 62 is not bonded to the runners 60 distal the shaft 50. With this construction, the overlay 62 allows the runners 60 to freely deflect or expand within the overlay 62, collectively forming and supporting the funnel shape in the expanded condition of FIG. 3C. While the overlay 62 can be elastically deformable, the overlay 62 provides resistance to continued deflection of the runners 60 beyond a certain level of deflection. Thus, the overlay 62 controls the length and angle of taper defined by the funnel segment 62 in the funnel shape of the expanded condition. The runners 60, in turn, create a columnar strength within the overlay 62, while still allowing the overlay 62, and thus the funnel segment 42, to expand.

Figure 4A:
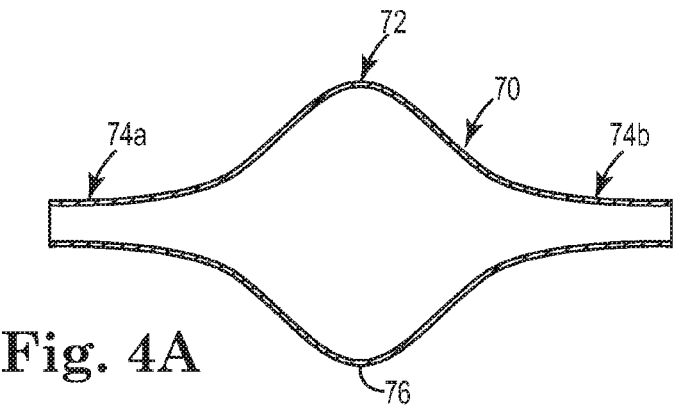
FIGS. 4A-4D illustrate construction of the recapture sheath of FIG. 3A in accordance with principles of the present disclosure.

In one embodiment, the overlay 62 is initially provided as a thin-walled balloon that is inverted onto itself to encompass the runners 60. For example, FIGS. 4A-4D illustrate construction of the funnel segment 42 (FIG. 3A) in accordance with some embodiments of the present disclosure. Initially, and as shown in FIG. 4A, a balloon 70 structure is formed or provided, having an intermediate section 72 and opposing first and second end sections 74a, 74b. The balloon structure 70 can be created, for example, by focused inflation of a polymer tube in a manner generating the intermediate section 72. The intermediate section 72 has enlarged inner and outer diameters as compared to the end sections 74a, 74b, tapering in diameter from a mid-point 76 to the end sections 74a, 74b. As a point of reference, the end sections 74a, 74b are optionally sized to fit the inner and outer diameters, respectively, of the shaft 50 (FIG. 3A) to which the overlay 62 will be attached. Thus, for example, where the shaft 50 is a 16 French sheath, the first end section 74a can be sized to approximate an outer diameter of a 16 French sheath, whereas the second end section 74b can be sized to approximate an inner diameter of a 16 French sheath (or vice-versa). The intermediate section 72 has a maximum diameter that is slightly larger than the outer diameter of the shaft 50 (e.g., where the shaft 50 is 16 French sheath, the maximum diameter of intermediate section 72 can be on the order 15-20 mm). Alternatively, other dimensions are also envisioned.

Figure 4B:
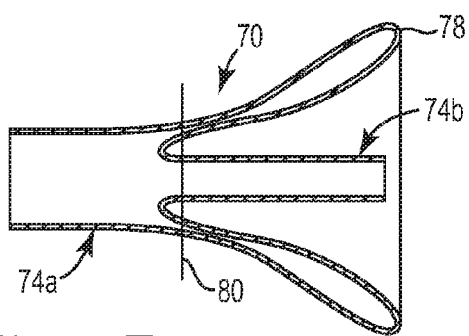

The balloon structure 70 is then inverted or folded into itself as shown in FIG. 4B. In particular, the second end section 74b is directed axially toward the first end section 74a, causing the intermediate section 72 to invert onto itself at approximately the mid-point 76 (FIG. 4A). A location of the inversion is referenced at 78 in FIG. 4B. The inverted balloon structure 70 is then cut along a cut line 80. The cut line 80 is located along a length of the inverted balloon structure 70 that corresponds with the inner and outer diameters of the shaft 50 (FIG. 3A), for example where an inner diameter of the first end section 74a approximates an outer diameter of the shaft 50 and an outer diameter of the second end section 74b approximates an inner diameter of the shaft 50.

Figure 4C:
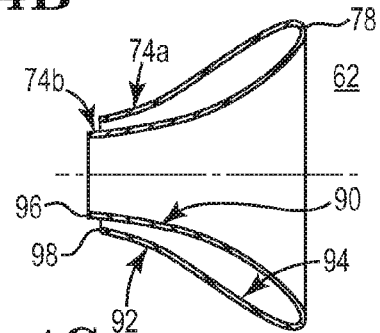

Once cut, the remaining portion of the second end section 74b is further inverted into the first end section 74a as shown in FIG. 4C. The resultant overlay 62 is defined by inner and outer tubular walls 90, 92 arranged to define an open space 94 therebetween. The walls 90, 92 extend from the inversion 78, with the inner wall 90 terminating at an inner end 96 having a diameter approximating an inner diameter of the shaft 50 (FIG. 3A) to which the overlay 62 is subsequently assembled. The outer wall 92 terminates at an outer end 98 opposite the inversion 78 and having a diameter approximating an outer diameter of the shaft 50.

Figure 4D:
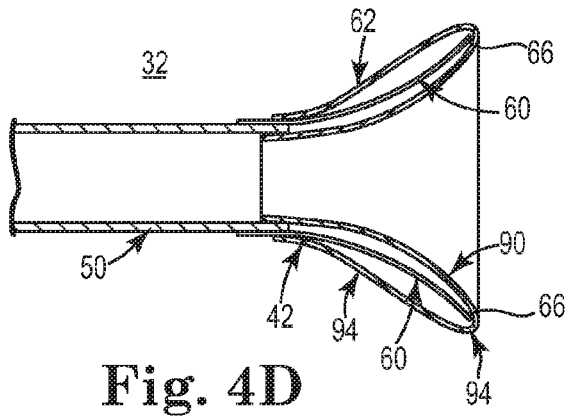

With reference to FIG. 4D, construction of the recapture sheath 32 includes the runners 60 attached to, and extending distally from, the shaft 50 as described above. The so-assembled runners 60 are then inserted into the open space 94 of the overlay 62. The overlay 62 is then bonded to the shaft 50. For example, the inner wall 90 can be thermally bonded to the inner diameter of the shaft 50. The outer wall 92 can similarly be thermally bonded to an outer diameter of the shaft 50 and/or to the first end 64 of each of the runners 60. However, the overlay 62 is not bonded to the runners 60 distal the shaft 50 in some embodiments. In other constructions, the overlay 62 may be bonded to a portion of one or more the runners 60 distal the shaft 50, but at least the distal tip 66 of each of the runners 60 is free of bonding to the overlay 62.

The shaft 50 can assume any forms appropriate for supporting the funnel segment 42 in a manner facilitating desired sliding movement of the funnel segment 42 in response to movement of the shaft 50. For example, the shaft 50 can be a thermoplastic elastomer tube, such as Pebax®, and optionally can include an embedded braided material layer (e.g., stainless steel wire).

The recapture sheath 32, and in particular the funnel segment 42, can be alternatively constructed in various other manners. For example, a thin-walled polymer tube can be wrapped about the runners 60. Regardless, upon final construction, the funnel segment 42 is transitionable from the normal condition of FIG. 3A to the expanded condition (and corresponding funnel shape) of FIG. 3C in response to an internal expansive force, and then self-transition back toward the normal condition once the internal expansive force is removed due, at least in part, to a shape memory attribute collectively imparted into the funnel segment 42 by the runners 60.

Returning to FIG. 2, the remaining components 34-38 of the delivery device 30 can assume a variety of forms appropriate for percutaneously delivering and deploying a stented self-expanding prosthetic heart valve. For example, the inner shaft assembly 34 can have various constructions appropriate for supporting a stented prosthetic heart valve within the capsule 40. In some embodiments, the inner shaft assembly 34 can include a retention member 100, an intermediate tube 102, and a proximal tube 104. In general terms, the retention member 100 can be akin to a plunger, and incorporates features for retaining the stented prosthetic heart valve within the capsule 40 as described below. The tube 102 connects the retention member 100 to the proximal tube 104, with the proximal tube 104, in turn, coupling the inner shaft assembly 34 with the handle 38. The components 100-104 can combine to define a continuous lumen 106 (referenced generally) sized to slideably receive an auxiliary component such as a guide wire (not shown).

The retention member 100 can include a tip 110, a support tube 112, and a hub 114. The tip 110 forms or defines a nose cone having a distally tapering outer surface adapted to promote atraumatic contact with bodily tissue. The tip 110 can be fixed or slideable relative to the support tube 112. The support tube 112 extends proximally from the tip 110 and is configured to internally support a compressed, stented prosthetic heart valve generally disposed thereover, and has a length and outer diameter corresponding with dimensional attributes of the selected prosthetic heart valve. The hub 114 is attached to the support tube 112 opposite the tip 110 (e.g., an adhesive bond), and provides a coupling structure 120 (referenced generally) configured to selectively capture a corresponding feature of the prosthetic heart valve. The coupling structure 120 can assume various forms, and is generally located along an intermediate portion of the inner shaft assembly 34. In some constructions, the coupling structure 120 includes one or more fingers sized to be received within corresponding apertures formed by the prosthetic heart valve stent frame (e.g., the prosthetic heart valve stent frame can form wire loops at a proximal end thereof that are received over respective ones of the fingers when compressed within the capsule 40). Other releasable coupling arrangements are also acceptable, such as the hub 114 forming one or more slots sized to slideably receive a corresponding component(s) of the prosthetic heart valve (e.g., a bar or leg segment of the stent frame). Further, the inner shaft assembly 34 can incorporate additional structures and/or mechanisms that assist in temporarily retaining the stented valve (e.g., a tubular sleeve biased over the coupling structure 120), such as described in U.S.

Provisional Application Ser. No. 61/237,373 entitled "Transcatheter Valve Delivery Systems and Methods" filed Aug. 27, 2009 and the entire teachings of which are incorporated herein by reference.

The intermediate tube 102 is formed of a flexible polymer material (e.g., PEEK), and is sized to be slideably received within the delivery sheath assembly 36. The proximal tube 104 can include, in some embodiments, a leading portion 122 and a trailing portion 124. The leading portion 122 serves as a transition between the intermediate and proximal tubes 102, 104 and thus in some embodiments is a flexible polymer tubing (e.g., PEEK) having a diameter slightly less than that of the intermediate tube 102. The trailing portion 124 has a more rigid construction, configured for robust assembly with the handle 38 such as a metal hypotube. Other constructions are also envisioned. For example, in other embodiments, the intermediate and proximal tubes 102, 104 are integrally formed as a single, homogenous tube or solid shaft.

The delivery sheath assembly 36 includes the capsule 40 and a delivery sheath shaft 130, and defines proximal and distal ends 132, 134. The capsule 40 extends distally from the delivery shaft 130, and in some embodiments has a more stiffened construction (as compared to a stiffness of the delivery shaft 130) that exhibits sufficient radial or circumferential rigidity to overtly resist the expected expansive forces of the stented prosthetic heart valve in the compressed arrangement. For example, the delivery shaft 130 can be a polymer tube embedded with a metal braiding, whereas the capsule 40 is a laser-cut metal tube that is optionally embedded within a polymer covering. Alternatively, the capsule 40 and the delivery shaft 130 can have a more uniform construction (e.g., a continuous polymer tube). Regardless, the capsule 40 is constructed to compressively retain the stented prosthetic heart valve at a predetermined diameter when loaded within the capsule 40, and the delivery shaft 130 serves to connect the capsule 40 with the handle 38. The delivery shaft 130 (as well as the capsule 40) is constructed to be sufficiently flexible for passage through a patient's vasculature, yet exhibit sufficient longitudinal rigidity to effectuate desired axial movement of the capsule 40. In other words, proximal retraction of the delivery shaft 130 is directly transferred to the capsule 40 and causes a corresponding proximal retraction of the capsule 40. In other embodiments, the delivery shaft 130 is further configured to transmit a rotational force or movement onto the capsule 40.

The handle 38 generally includes a housing 140 and one or more actuator mechanisms 142 (referenced generally). The housing 140 maintains the actuator mechanism(s) 142, with the handle 38 configured to facilitate sliding movement of the delivery sheath assembly 36 relative to the recapture sheath 32 and the inner shaft assembly 34, as well as the recapture sheath 32 relative to the inner shaft assembly 34 and the delivery sheath assembly 36. The housing 140 can have any shape or size appropriate for convenient handling by a user. In one simplified construction, a first, deployment actuator mechanism 142a includes a user interface or actuator 144 slideably retained by the housing 140 and coupled to a delivery sheath connector body 146. The proximal end 132 of the delivery sheath assembly 36 is connected to the delivery sheath connector body 146. The inner shaft assembly 34, and in particular the proximal tube 104, is slideably received within a passage 148 (referenced generally) of the delivery sheath connector body 146, and is rigidly coupled to the housing 140. A second, recapture actuator mechanism 142b (referenced generally) similarly includes a user interface or actuator 150 movably maintained by the housing 140 and coupled to the recapture sheath 32 via one or more bodies (not shown) facilitating movement of the recapture sheath 32 with operation of the recapture actuator 150. With this but one acceptable construction, the deployment actuator 144 can be operated to effectuate axial movement of the delivery sheath assembly 36 relative to the recapture sheath 32 and the inner shaft assembly 34. Similarly, the recapture actuator 150 can be manipulated to axially slide the recapture sheath 32 relative to the inner shaft assembly 34 and the delivery sheath assembly 36.

FIG. 5A illustrates, in simplified form, a system 158 in accordance with the present disclosure for restoring (e.g., replacing or repairing) a defective heart valve of a patient and including a stented prosthetic heart valve 160 loaded within the delivery device 30. In the delivery state of the delivery device 30 of FIG. 5A, the prosthetic heart valve 160 is crimped over the inner shaft assembly 34, such that the prosthetic heart valve 160 engages the coupling structure 120. The capsule 40 compressively contains the prosthetic heart valve 160 in the compressed arrangement shown to define a loaded mode of the system 158 (it being understood that the "loaded mode" of the system 158 corresponds with the delivery device 30 in the delivery state). Finally, the distal end 54 of the recapture sheath 32 is longitudinally spaced from the prosthetic heart valve 160, with the funnel segment 42 assuming the normal condition described above. For example, with the arrangement of FIG. 5A, the recapture sheath distal end 54 is proximally spaced from the prosthetic heart valve 160. As implicated by FIG. 5A, then, the capsule 40 exhibits sufficient structural integrity to compressively maintain the prosthetic heart valve 160 in the compressed arrangement without the funnel segment 42, or any other portion of the recapture sheath 32, being disposed over the prosthetic heart valve 160 in the loaded mode.

To deploy the prosthetic heart valve 160 from the delivery device 30 (i.e., a deployment mode of the system 158), the delivery sheath assembly 36 is withdrawn from over the prosthetic heart valve 160, for example by proximally retracting the capsule 40, such that the capsule distal end 134 is proximal the coupling structure 120. Once the capsule 40 is proximal the coupling structure 120, the prosthetic heart valve 160 is allowed to self-expand to the natural arrangement thereby releasing from the delivery device 30.

In some instances, a clinician may desire to only partially deploy the prosthetic heart valve 160 from the delivery device 30 and then evaluate before fully releasing the prosthetic heart valve 160. For example, the delivery device 30 loaded with the prosthetic heart valve 160 can be employed as part of a method to repair a damaged heart valve of a patient. Under these circumstances, the delivery device 30, in the delivery state, is advanced toward the native heart valve implantation target site, for example in a retrograde approach, through a cut-down to the femoral artery and into the patient's descending aorta. The delivery device 30 is then advanced, under fluoroscopic guidance, over the aortic arch, through the ascending aorta, and midway across the defective aortic valve (for aortic valve replacement). Once positioning of the delivery device 30 is estimated, the delivery sheath assembly 36, and in particular the capsule 40, is partially retracted relative to the prosthetic heart valve 160 as shown in FIG. 5B. A distal region 170 of the prosthesis 160 is thus exteriorly exposed relative to the capsule 40 and self-expands. In the partially deployed mode of FIG. 5B, however, at least a proximal region 172 of the prosthesis 160 remains within the confines of the capsule 40, and thus coupled to the delivery device 30. In this partially deployed state of the delivery device 30, a position of the stented prosthetic heart valve 160 relative to the desired implantation site can again be evaluated.

In the event the clinician believes, based upon the above evaluation, that the prosthesis 160 should be repositioned relative to the implantation site, the prosthetic heart valve 160 must first be contracted and "resheathed" by transitioning the delivery device 30 to a recapturing state (and thus of the system 158 to a recapturing mode). As shown in FIG. 5C, the recapture sheath 32 is distally advanced relative to the delivery sheath assembly 36. In particular, the funnel segment 42 is distally advanced beyond the distal end 134 of the capsule 40, and maneuvered into contact with the exposed distal region 170 of the prosthetic heart valve 160. The overlay 62 (FIG. 3A) readily slides along a surface of the prosthetic heart valve 160, with the distal end 54 gently engaging the distal region (due, at least in part, to the thin wall thickness and expansibility of the distal end 54). Further, as the funnel segment 42 contacts or interfaces with the distally expanding diameter rigidly defined by the distal region 170, the funnel segment 42 transitions to the expanded condition. In particular, the runners 60 (FIGS. 3A-3C) deflect radially outwardly in response to an interface between the distal tips 66 (FIG. 3A) and the enlarged diameter distal region 170 of the prosthetic heart valve 160. Stated otherwise, the distal region 170 generates an internal expansive force within the funnel segment 42. The overlay 62 generally permits necessary deflection to accommodate a diameter of the prosthetic heart valve 160, but generally controls or maintains the funnel segment 42 to a funnel shape.

Distal advancement of the funnel segment 42 continues along approximately an entirety of the prosthetic heart valve 160 as shown in FIG. 5D. While the distal region 170 may or may not slightly compress in response to placement within the funnel segment 42, complete compression of the prosthetic heart valve 160 does not occur. Instead, as shown in FIG. 5E, the delivery sheath assembly 36 is subsequently distally advanced, with the capsule 40 sliding over and along the funnel segment 42. The funnel segment 42 effectively serves to physical isolate the capsule 40 from directly contacting the prosthetic heart valve 160. As a result, the distal end 134 of the capsule 40 does not abruptly contact the prosthetic heart valve 160 in a manner that might otherwise cause the capsule 40 to buckle or collapse. However, the capsule 40 overcomes the radial force of the distal region 170 and acts to radially compress the previously-expanded distal region 170, forcing the prosthetic heart valve 160 back to approximately the initial, collapsed arrangement as shown in FIG. 5E.

Once the prosthetic heart valve 160 is resheathed or recaptured, the delivery device 30 can be repositioned relative to the implantation site, and the process repeated until the clinician is comfortable with the achieved positioning. Alternatively, the resheathed stented prosthetic heart valve 160 can be removed from the patient.

Figure 6:
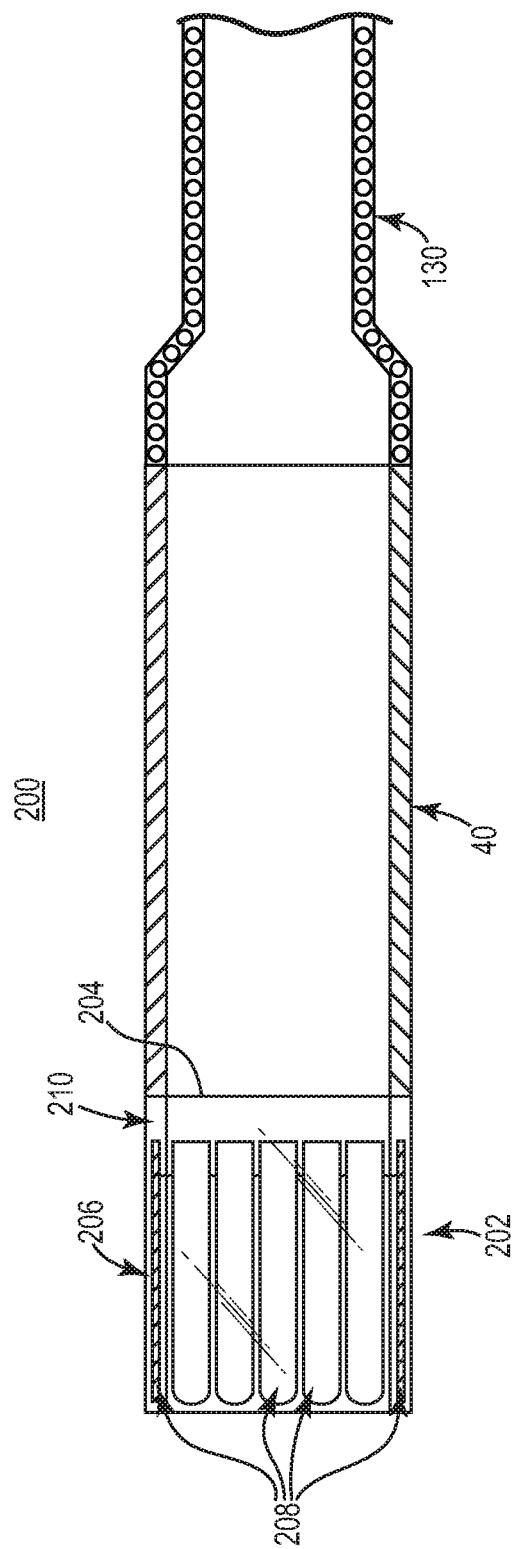
FIG. 6 is a simplified cross-section view a delivery sheath assembly incorporating a recapture sheath funnel segment and useful with delivery devices in accordance with principles of the present disclosure.

While the recapture sheath 32 has been described as being a component apart from the delivery sheath assembly 36, in other constructions, the components can be combined. For example, FIG. 6 illustrates an alternative delivery sheath assembly 200 useful with a percutaneous prosthetic heart valve delivery device in accordance with principles of the present disclosure. The delivery sheath assembly includes the capsule 40 and the delivery sheath shaft 130 as described above with respect to the delivery sheath assembly 36 (FIG. 2). In addition, a recapture sheath 202 is attached to, and extends distally from, a distal end 204 the capsule 40. The recapture sheath 202 can assume any of the forms described above with respect to the recapture sheath 32 (FIG. 2), and generally includes a funnel segment 206. As with the funnel segment 42 (FIGS. 3A-3C), the funnel segment 206 is configured to have a normal or relaxed condition characterized by a substantially cylindrical shape, and is transitionable to an expanded condition characterized by a funnel-like shape having a distally increasing diameter. Further, the funnel segment 206 is configured to self-transition from the expanded condition back to or toward the normal condition. Thus, the funnel segment 206 can include a plurality of circumferentially spaced runners 209 (akin to the runners 60 of FIGS. 3A-3C) surrounded by a polymer overlay 210 (akin to the overlay 62 of FIGS. 3A-3C) as described above, with the runners 208 collectively imparting a shape memory attribute to the funnel segment 206 toward the normal condition.

FIG. 7 illustrates the delivery sheath assembly 200 as part of a delivery device 220 loaded with the prosthetic heart valve 160 to define a system for repairing (e.g., replacing) a defective valve. In the delivery state of FIG. 7, the capsule 40 is disposed over the prosthetic heart valve 160, compressively retaining the prosthetic heart valve 160 in crimped engagement with the inner shaft assembly 34 as described above. The funnel segment 206 is longitudinally spaced from the prosthetic heart valve 160. In particular, with the construction of FIG. 7, the delivery state of the delivery device 220 (i.e., the loaded mode of the repair system) includes the funnel segment 206 being located distal the prosthetic heart valve 160. The shape memory feature imparted to the funnel segment 206 causes the funnel segment 206 to naturally retain the reduced diameter normal condition illustrated.

Figure 8B:
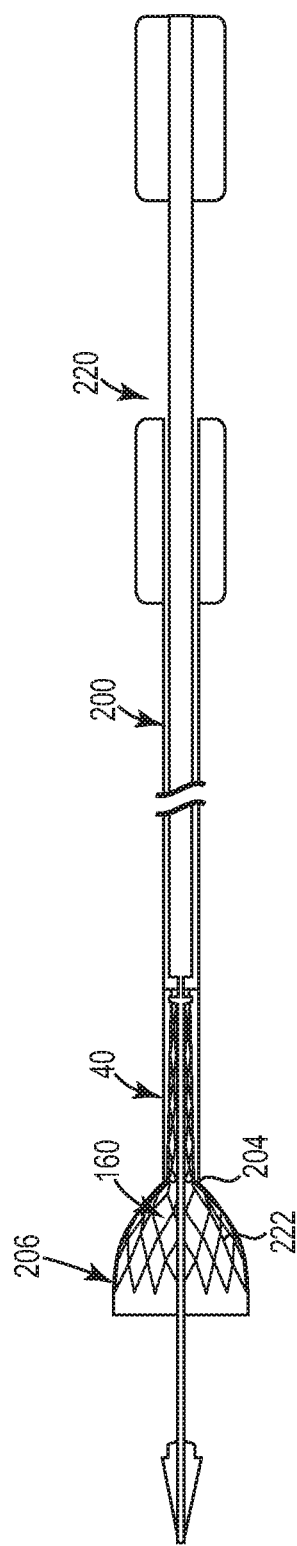

Partial deployment of the prosthetic heart valve 160 from the delivery device 220 is illustrated in FIG. 8A, and includes partially withdrawing the capsule 40 from the prosthetic heart valve 160. In particular, the capsule 40 is proximally retracted. The funnel segment 206 simultaneously moved proximally with refraction of the delivery sheath assembly 200. As illustrated, a distal region 222 of the prosthetic heart valve 160 distal the distal end 204 capsule 40 is no longer compressively constrained by the capsule 40, and begins to self-expand. The funnel segment 206 does not overtly resist or impede this expansion. Instead, the funnel segment 206 expands (i.e., is forcibly transitioned to the expanded condition) to a shape generally corresponding with that of the deploying distal region 222.

Where desired, the prosthetic heart valve 160 can be resheathed or recaptured within the capsule 40 by distally advancing the delivery sheath assembly 200 as generally reflected by the recapturing state of the delivery device 220 in FIG. 8B. In this regard, the funnel segment 206, in the expanded condition, readily slides along an exterior of the prosthetic heart valve 160, and effectively serves as a buffer between the structure of the prosthetic heart valve 160 and the stiff, distal end 204 of the capsule 40. As a result, the capsule 40 will not buckle as it is advanced over the distal region 222, nor will the capsule 40 damage the prosthetic heart valve 160. Instead, as the capsule 40 is distally advanced over the distal region 222, the prosthetic heart valve 160 is forcibly compressed back to the initial, compressed arrangement (FIG. 8A). As a point of reference, as the funnel segment 206 is maneuvered distal the prosthetic heart valve 160, the shape memory attribute causes the funnel segment 206 to self-transition back toward the reduced diameter, normal condition.

The delivery devices shown and described herein can be modified for delivery of balloon-expandable stented prosthetic heart valves, within the scope of the present disclosure. That is to say, delivering balloon-expandable stents to an implantation location can be performed percutaneously using modified versions of the delivery devices of the present disclosure. In general terms, this includes providing a transcatheter assembly that can include a delivery sheath and/or additional sheaths as described above. The devices would further include a delivery catheter, a balloon catheter, and/or a guide wire. A delivery catheter used in this type of delivery device defines a lumen within which the balloon catheter is received. The balloon catheter, in turn, defines a lumen within which the guide wire is slideably disposed. Further, the balloon catheter includes a balloon that is fluidly connected to an inflation source. With the stented valve mounted to the balloon, the transcatheter assembly is delivered through a percutaneous opening in the patient via the delivery device. Once the stented prosthetic heart valve is properly positioned, the balloon catheter is operated to inflate the balloon, thus transitioning the stented prosthesis to an expanded arrangement.

The systems, devices, and methods of the present disclosure provide a marked improvement over previous designs. By providing an expandable recapture sheath apart from the delivery sheath capsule otherwise utilized to compressively retain the stented prosthetic heart valve, a partially deployed prosthesis is more readily recaptured.

Although the present disclosure has been described with reference to preferred embodiments, workers skilled in the art will recognize that changes can be made in form and detail without departing from the spirit and scope of the present disclosure.

What is claimed is:

1. A method of deploying a stented prosthetic heart valve to an implantation site, the method comprising:
    receiving a delivery device loaded with a radially expandable prosthetic heart valve having a stent frame to which a valve structure is attached, the delivery device including a delivery sheath capsule containing the prosthetic heart valve in a compressed arrangement over an inner shaft assembly in a delivery state of the device, and a recapture sheath including a funnel segment slidably disposed over the inner shaft assembly, the funnel segment being longitudinally spaced from the prosthetic heart valve in the delivery state;
    delivering the prosthetic heart valve in the compressed arrangement through a bodily lumen of the patient and to the implantation site via the delivery device in the delivery state;
    proximally retracting the capsule segment relative to the prosthetic heart valve such that a distal region of the prosthetic heart valve is exposed distal the capsule, wherein the distal region self-expands toward a deployed arrangement;
    evaluating a position of the prosthetic heart valve relative to the implantation site;
    distally advancing the recapture sheath relative to the prosthetic heart valve such that the funnel segment is distal the capsule and expands to a funnel shape in response to contact with the distal region of the prosthetic heart valve;
    distally advancing the funnel segment over the distal region of the prosthetic heart valve;
    arranging the capsule over the prosthetic heart valve to cause the distal region of the prosthetic heart valve to transition toward the collapsed arrangement within the capsule; and
    fully proximally retracting the capsule and the funnel segment from the prosthetic heart valve such that the prosthetic heart valve self-deploys from the inner shaft assembly.

2. The method of claim 1, wherein the delivery sheath capsule is provided as part of a delivery sheath assembly further including a delivery sheath shaft, and further wherein the recapture sheath is slidably disposed between the delivery sheath assembly and the inner shaft assembly.

3. The method of claim 2, wherein distally advancing the recapture sheath includes sliding the recapture sheath relative to the delivery sheath assembly.

4. The method of claim 3, wherein arranging the capsule over the prosthetic heart valve to recapture the prosthetic heart valve includes sliding the capsule over the funnel segment.

5. The method of claim 1, wherein the recapture sheath shaft is formed as a distal extension from the capsule such that the capsule and the recapture sheath are slidably fixed to one another.

6. The method of claim 5, wherein distally advancing the recapture sheath includes distally advancing the delivery sheath assembly.

7. The method of claim 6, wherein arranging the capsule over the prosthetic heart valve to recapture the prosthetic heart valve includes sliding the funnel segment distally beyond the prosthetic heart valve.

* * * * *